United States Patent [19]
Jaffrezic-Renault et al.

[11] Patent Number: 5,350,701
[45] Date of Patent: Sep. 27, 1994

[54] PROCESS FOR PRODUCING A SURFACE GATE OF AN INTEGRATED ELECTRO-CHEMICAL SENSOR, CONSISTING OF A FIELD-EFFECT TRANSISTOR SENSITIVE TO ALKALINE-EARTH SPECIES AND SENSOR OBTAINED

[75] Inventors: Nicole Jaffrezic-Renault, Ecully; Jean-Marc Chovelon, Lyons; Hubert Perrot, Saint Martin D'Auxigny; Pierre Le Perchec, Lyons; Yves Chevalier, Irigny, all of France

[73] Assignee: Ecole Centrale de Lyon, Ecully Cedex, France

[21] Appl. No.: 988,912

[22] PCT Filed: Sep. 13, 1991

[86] PCT No.: PCT/FR91/00723

§ 371 Date: May 6, 1993

§ 102(e) Date: May 6, 1993

[87] PCT Pub. No.: WO92/05435

PCT Pub. Date: Apr. 2, 1992

[30] Foreign Application Priority Data

Sep. 14, 1990 [FR] France ................... 9011586

[51] Int. Cl.$^5$ ............... H01L 21/335; G01N 27/414
[52] U.S. Cl. ................................. 437/40; 437/1; 437/59; 204/416; 204/418
[58] Field of Search ............ 437/40, 59, 1; 204/418, 204/416

[56] References Cited

U.S. PATENT DOCUMENTS

| 4,514,263 | 4/1985 | Janata ................... 204/416 |
| 5,011,589 | 4/1991 | Amemiya et al. ........... 204/416 |
| 5,077,229 | 12/1991 | Forlani ................... 437/40 |

FOREIGN PATENT DOCUMENTS

| 0375070 | 6/1990 | European Pat. Off. . |
| 0203979 | 11/1983 | Fed. Rep. of Germany ...... 204/418 |
| 1155928 | 5/1985 | U.S.S.R. ................ 204/418 |

OTHER PUBLICATIONS

Shindengen, *Patent Abstracts of Japan*, 6, No. 195, Oct. 5, 1982; JA 57-104852.
Aktik et al., *J. Appl. Phys.*, 51 (9), Sep. 1980, pp. 5055–5057.

Primary Examiner—T. N. Quach
Attorney, Agent, or Firm—Bacon & Thomas

[57] ABSTRACT

A process for producing a surface gate comprising a selective membrane for an integrated chemical sensor comprising a field effect transistor, and the integrated chemical sensor thus produced, wherein the surface gate is particularly sensitive to alkaline-earth species, and more particularly, sensitive to the calcium ion. The process comprises forming grafts on the surface gate, and making the grafts operative utilizing phosphonate-based, iono-sensitive molecules.

10 Claims, 3 Drawing Sheets

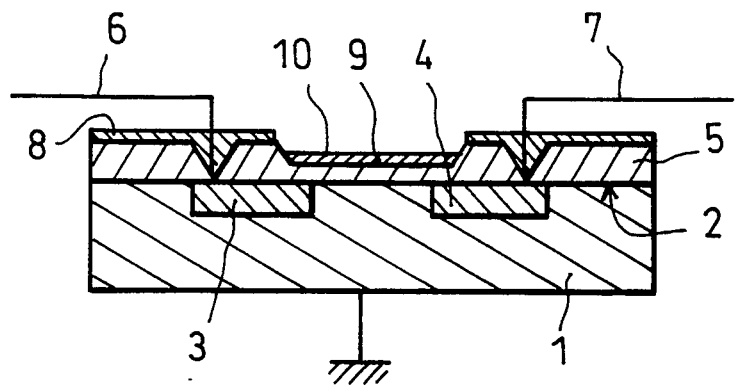
fig_1
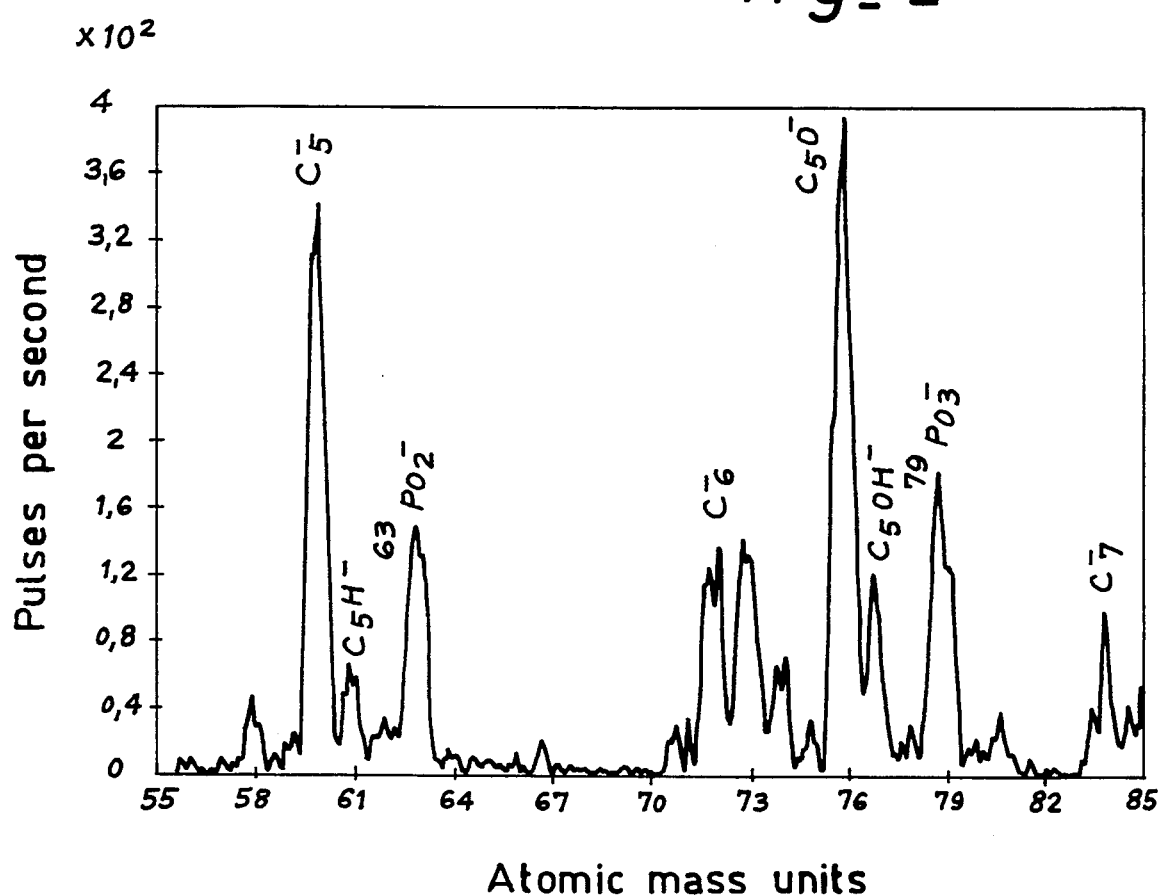
fig_2

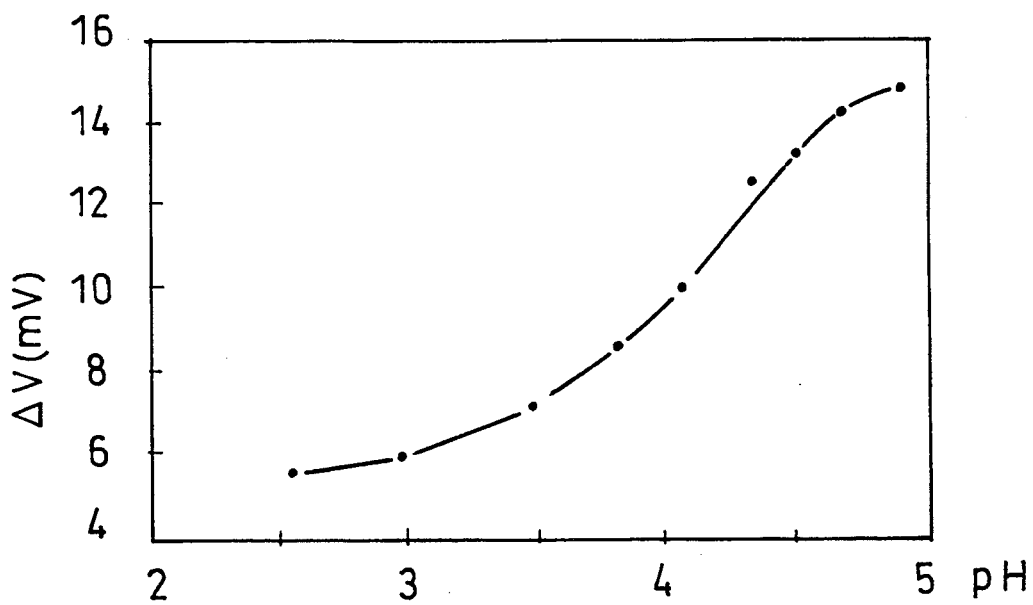
fig_3
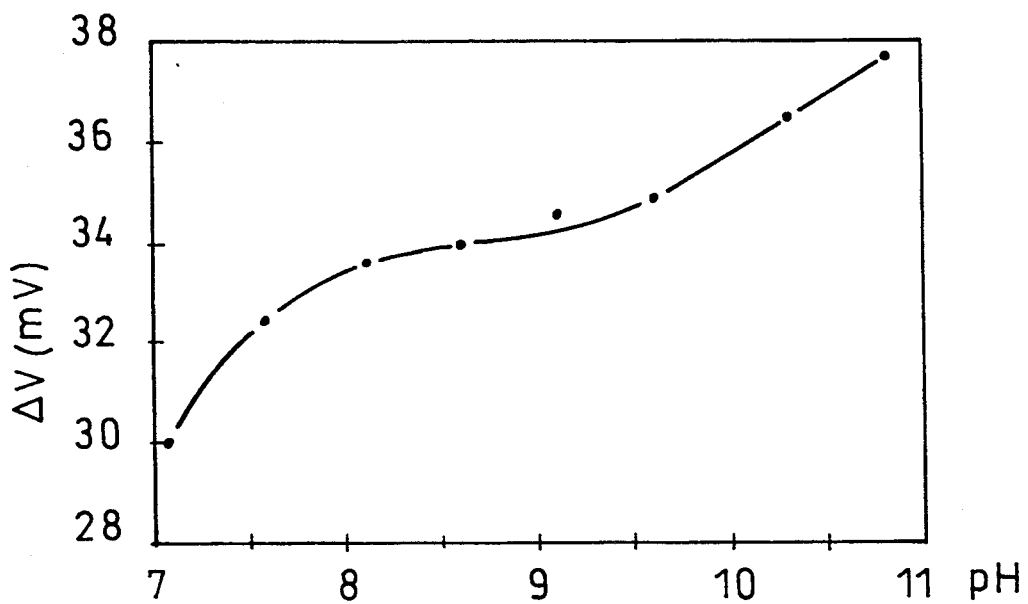
fig_4

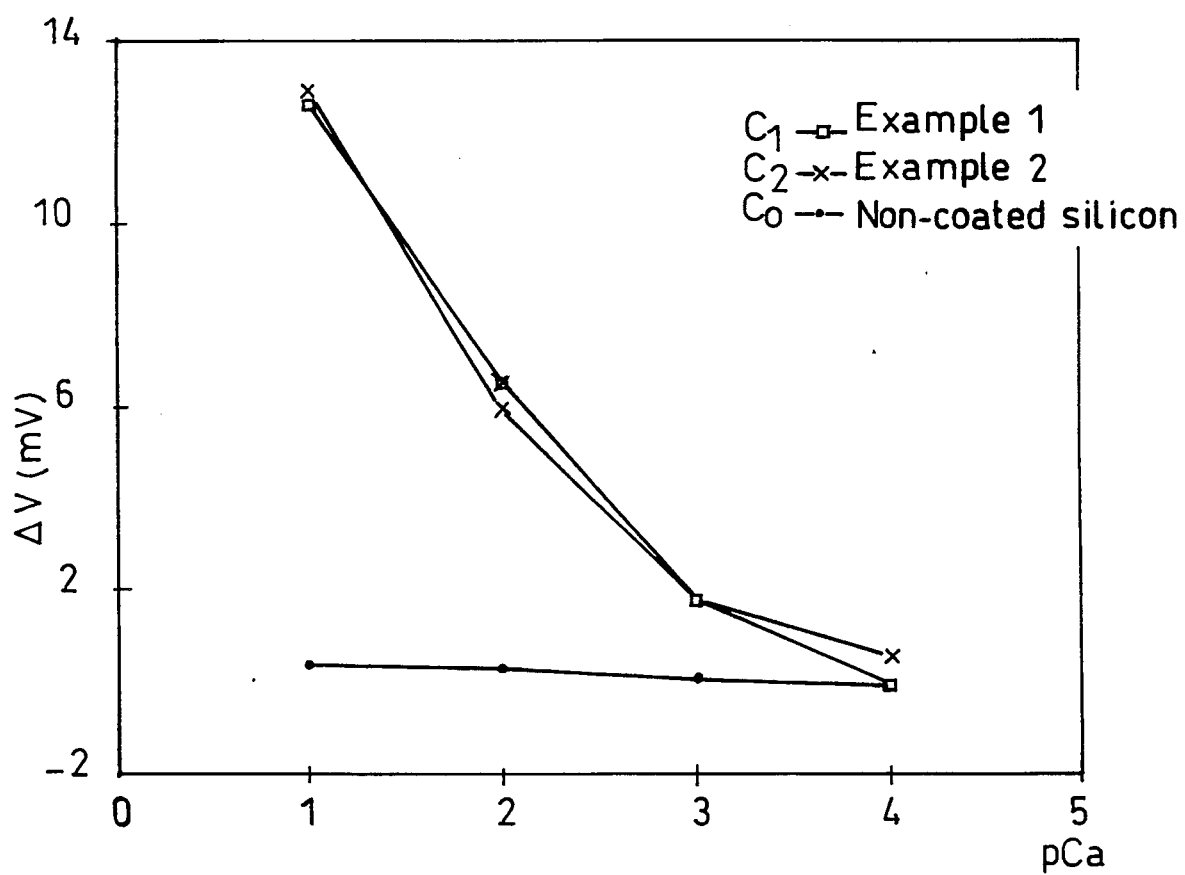
fig_5

PROCESS FOR PRODUCING A SURFACE GATE OF AN INTEGRATED ELECTRO-CHEMICAL SENSOR, CONSISTING OF A FIELD-EFFECT TRANSISTOR SENSITIVE TO ALKALINE-EARTH SPECIES AND SENSOR OBTAINED

FIELD OF THE INVENTION

The present invention relates to an integrated chemical sensor, comprising a field-effect transistor in which the metal gate is replaced by a selective membrane of the ionic species to be dosed and placed in contact with the solution to be analyzed.

Such sensors result from the evolution or development of the properties of the field-effect transistors comprising, in a semi-conducting substrate, two doped zones, called source and drain, and, in a layer of a dielectric material covering the semi-conductor and the doped zones, a central zone covered by a gate whose variable electrical supply makes it possible to modulate the passage of the current between the source and the drain.

DESCRIPTION OF THE RELATED ART

In publication IEEE TRANS, BIOMED. Eng. BME, 17 (1970) 70, P. BERGVELD proposed eliminating the gate and placing the surface of the dielectric material directly in contact with an electrolytic solution containing $H^+$ and $OH^-$ ions and in which a polarization electrode is immersed. For a given polarization, a drain current is obtained, representative of the concentration of the electrolytic solution. Any modification of concentration modulates the drain current. The transistor then functions as an integrated chemical sensor.

In order to broaden the domain of application limited to the medium containing H ions, it has been proposed to interpose an iono-sensitive surface gate between the electrolytic solution and the surface of the dielectric material. Such a surface gate may comprise an organic or inorganic membrane, connected by gluing, by supply or by chemical deposit in vacuo. Such a method makes it possible to produce a surface gate specific to a product and thus capable of analysis of the latter in a specific medium.

Such a development has brought a certain advantage with respect to broadening of the range of application, but is not entirely satisfactory, due to ageing of the added organic or inorganic membrane, which lacks reliability over time.

In order to overcome this problem, it has been proposed, particularly in Application FR-2 600 212 (86-08989), to make a directly integrated sensitive surface gate with the objective of eliminating the presence of the added membrane. According to this technique, the surface gate is subjected directly to a treatment of hydroxidation, then to a treatment of impregnation with a solution of silane, followed by condensation of the silane.

This technique is satisfactory but may be considered as being of limited application, due to the necessity of having available, for the phase of impregnation, a silane in solution incorporating the group specific to the sensitivity to be given to the surface gate being treated.

Furthermore, it has been determined that such a technique does not allow maximum performance to be obtained, particularly for certain specific sensitivities, such as those to alkaline-earth species and, more particularly, to the calcium ion.

Now, such sensors are a subject of real need in numerous applications requiring electrochemical analysis, including big-medical analysis, water hardness testing, agronomy (analysis of nutritive solutions), and the environment (analysis of fresh- and sea-water).

SUMMARY OF THE INVENTION

The object of the present invention is to solve the above problem by proposing a novel process for making, on an electrochemical sensor, a selective surface gate particularly sensitive to alkaline-earth species, and more particularly, to the calcium ion, and wherein the operational characteristics of the sensors are reliable over time and allow a thorough miniaturization of sensors comprising a selective surface gate.

The invention comprises a process for making a surface gate of an integrated electrochemical sensor comprising a field-effect transistor having two doped zones, wherein the doped zones are a source and a drain, and having a surface on which a surface gate is to be formed, wherein the process comprises the steps of: subjecting the surface to a treatment of hydroxylation in order to obtain $10^{14}$ to $10^{15}$ OH sites per $cm^2$, washing and drying the surface, and further comprising the steps of: grafting the surface with a grafting product in order to produce grafts on some or all sites on the surface, preparing phosphonate-based iono-sensitive molecules, and making operative one or more of the grafts using the iono-sensitive molecules.

Another object of the invention is an integrated electrochemical sensor having a surface gate obtained by carrying out the process described herein.

In order to attain the above objectives, the process according to the invention comprises the following steps:

effecting grafting of the surface with a grafting product, for the purpose of producing grafts on at least certain sites on the surface, preparing phosphonate-based iono-sensitive molecules, making operative some or all of the grafts using the iono-sensitive molecules.

Various other characteristics will appear from the description made hereinbelow with reference to the accompanying drawings which show, by way of non-limiting examples, embodiments of the object of the invention.

BRIEF DESCRIPTION OF THE DRAWINGS

FIG. 1 is a schematic view of an integrated chemical sensor with a sensitive surface gate according to the invention.

FIGS. 2 to 5 are curves illustrating the structural and functional characteristics of sensors according to the invention.

DESCRIPTION OF THE PREFERRED EMBODIMENTS

FIG. 1 shows an integrated chemical sensor comprising a substrate 1 made of a semi-conducting material having undergone, from the surface 2, a doping operation, for the purpose of defining two zones 3 and 4 intended to comprise, respectively, a source and a drain. The surface 2 is coated with a layer 5 of silica of electronic quality. The layer 5, before or after the establishment of contacts 6 and 7 with the source and the drain, is coated with a mask 8 over the whole of its surface, apart from that part having to correspond to the establishment of a surface gate located, in superposition of planes, in the central part between the source 3 and the drain 4.

The uncovered part of the layer 5 may be used as such or be treated, so as to obtain a layer 9 of a dielectric gate material, such as oxidized silicon nitride or oxynitride of silicon, of thickness in the range of 300 to 2500 Å (30 to 250 nanometers).

The process according to the invention employs further operational phases or steps, of which the principal ones are:

(I) a phase of grafting of grafts on some or all sites on the surface of the layer 5 or 9 of dielectric gate material, (II) a phase of preparation of iono-sensitive molecules adapted subsequently to ensure a sensitivity to the alkaline earth species and, more particularly, to the calcium ion, (III) a phase of making operative such grafts by the iono-sensitive molecules.

Phase (I)

Phase (I) for grafting the grafts comprises, according to a first variant, a preparatory step comprising hydroxylating the surface 10 in order to obtain from $10^{14}$ to $10^{15}$ OH sites per cm² of surface. This step of hydroxylation may be conducted by pickling from a basic aqueous solution containing sodium hydroxide, at a concentration of 0.1 to 1M. This step 1 may be conducted by immersion for a duration of time in the range of 5 to 30 minutes, the pickling solution being maintained at a temperature in the range of 15° to 40° C.

This step of hydroxylation may also be conducted, in the case of the layer 5 comprising silica alone, by a hydration consisting in placing the surface 10 in contact with bidistilled water maintained at a temperature of 95° C. Such hydration is continued for a duration of time in the range of 1 to 48 hours. A preferred embodiment continues the hydration for 12 hours.

Hydroxylation is then followed by a washing of the surface 10 by immersion or flow of a flux of distilled water delivered at ambient temperature.

Another variant embodiment of phase (I) of grafting a graft comprises, for the purpose of obtaining the same number of OH sites, in ensuring hydroxylation from a sulfochromic mixture (attack solution) composed of 1 ml of a saturated solution of potassium dichromate and 20 ml of concentrated (95-97%) sulfuric acid. This step may be conducted by immersion in the attack solution for a duration of time in the range of 1 to 5 minutes, the attack solution being maintained at a temperature in the range of 15° to 35° C.

This step of hydroxylation may be conducted in several steps, as described below:

Immersion in the attack solution previously described (sulfochromic mixture) under the same conditions, Immersion in ultra-pure water of resistance 18 megohms for a duration of time in the range of 10 to 15 hours, at a temperature in the range of 15° to 35° C.

Immersion in the attack solution previously described (sulfochromic mixture) under the same conditions.

Drying is then effected in the two embodiments, for example by means of a flux of inert gas at ambient temperature.

The preparatory step is then terminated and the surface 10 is subjected to degassing in vacuo between 1 and 5 Pa, preferably. 1 Pa, by heating the surface 10 to a temperature in the range of 120° to 160° C. and, preferably at 140° C. Such a degassing in vacuo is established for a duration of 1 to 5 hours, preferably limited to 2 hours, to obtain a completely dehydrated and degassed surface 10.

The grafting phase is then carried out by causing to react, by immersion, the surface 10 in a grafting product such as a pure, mono or multifunctional silane, an aminosilane, an alkoxysilane or a halosilane, intended to constitute on at least certain of the sites of the grafts, of general formula:

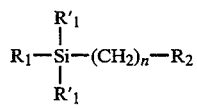

in which:
- $R_1$ is either
- $-(CH_3)_2-N-$,
- $-CH_3-O-$,
- $-CH_3-CH_2-O-$,
- $-Cl-$,
- $R'_1$ is either:
- $-CH_3-$,
- $-CH_3-O-$,
- $-CH_3-CH_2-O-$,
- $R_2$ is in all cases:
- $-Cl$.

so as to make the grafts operative. The silane is grafted by subjecting the surface 10 to a heating step in the temperature range of 60°-80° C. for a duration of 15 to 48 hours, preferably 70° C. for 48 hours, in an enclosure at ambient pressure, in the presence of an inert (neutral) gas, such as nitrogen or argon. The grafted surface 10 is then washed with a solvent of the silane in excess, such as ether, tetrahydrofuran, by immersion or flow at ambient temperature and preferably by renewing the solvent one to four times. A rate of grafting of the OH sites in the range of 1 to 50% of the sites present is obtained.

The grafted surface 10 is then subjected to a drying step in a flux of inert gas at ambient temperature.

An example of carrying out this phase of grafting of a chloropropyldimethyl chlorosilane is illustrated hereinafter by formulae (i) and (ii).

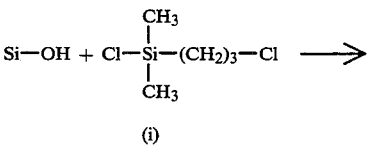

(i)

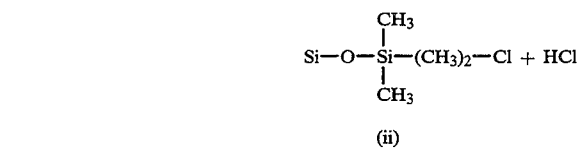

(ii)

Phase II

Phase (II), which involves the preparation of iono-sensitive molecules, comprises providing the molecules with the following characteristics:

a) presence of a group $(CH_3)_2-N-$ serving to ensure the chemical reaction of making operative the graft on the surface gate 10 treated, b) presence of a spacer group $-(CH_2)_n-$, c) presence of a group containing phosphorus-oxygen bonds and selected from:

| phosphonate | $-PO_3^{2-}$ |
|---|---|
| ethylphosphonate | $-PO_3Et^-$ |
| phosphate | $-O-PO_3^{2-}$ |

Examples of the preparation of iono-sensitive molecules are given hereinafter.

EXAMPLE 1

3-Dimethylamine propylphosphonate of sodium:

A mixture of 668 g (3.3 moles) of 1-3-dibromopropane and of 55 g (0.33 mole) of triethylphosphite is heated to 150° C. for 30 minutes. The excess of 1-3-dibromopropane is distilled in vacuo and makes it possible to obtain an intermediate product (A) of 85 g (0.33 mole) of formula:

$$Br-(CH_2)_3-PO_3Et_2$$

A mixture of 85 g of (A) and of 75 g (0.66 moles) of dimethylamine in aqueous (40%) solution and of 48 g (0.33 mole) of potassium carbonate is heated to 60° C. for 12 hours. The insoluble parts are filtered and the solvent evaporated in vacuo. A water-ether extraction makes it possible to isolate in the ether phase 49 g (0.22 mole) of a product (B) of formula $$(CH_3)_2-N-(CH_2)_3-PO_3 Et_2$$

An acid hydrolysis of product (B) is then carried out by refluxing in a 48% hydrobromic acid solution for 20 hours. The solvent is evaporated, then the residue is neutralized, with a sodium hydroxide solution, up to complete neutralization (pH = 12), to obtain the iono-sensitive molecules of formula:

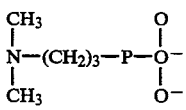

EXAMPLE 2

Dimethylamino methylphosphonate of sodium:

A solution of 21.6 g (0.48 mole) of dimethylamine in 70 g anhydrous ethanol is made by bubbling gaseous dimethylamine in ethanol. Next, 14.4 g (0.48 mole) of paraformaldehyde and 66.2 g (0.48 mole) of diethylphosphite are added to the solution, and the mixture is heated to 70° C. for 2 hours.

An acid hydrolysis is carried out by refluxing the mixture in a 48% solution of hydrobromic acid for 20 hours. After evaporation of the solvent, the residue is neutralized by a sodium hydroxide solution up to complete neutralization (pH=12), and comprises the iono-sensitive molecules of formula:

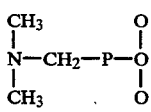

Phase (III)

Phase (III) of making the graft operative consists in placing about 0.5 g of the iono-sensitive molecules according to Example 1 or 2 in 40 ml of methanol in order to obtain a reactive sensitization mixture. The surface 10, treated as stated previously, is placed in contact with the mixture, which is taken to reflux of the methanol, i.e. at about 65° C. for a duration of 1 to 5 days.

Surface 10 is then rinsed with water and dried in a flux of an inert gas at ambient temperature, resulting in 1 to 100% of the grafted sites being made operative.

According to another embodiment of the invention, 100 to 500 mg of sodium iodide are added to the mixture to accelerate the reaction or to increase the percentage of the grafted sites made operative.

A surface 10, treated in accordance with the three phases described hereinabove with iono-sensitive molecules according to Example 1, has been the subject matter of a test of characterization by means of a mass spectrometer of secondary ions. The mass spectrometer features high lateral resolution, and is equipped for electronic imagery and for analysis of the insulants, and is capable of attaining a depth of analysis of the order of 10 to 20 Å (1 to 2 nanometers).

Such a spectrometer was of the SIMS-LAB type manufactured by VG INSTRUMENT equipped with a MIG 300 source.

An extreme surface elementary analysis test was conducted on a square surface with sides measuring 20 micrometers. The density of the current applied was of the order of $10^{-7}$ A/cm$^2$, for the purpose of creating a very low speed of abrasion, while presenting a sufficient sensitivity for a detection of the ionic species characteristic of chlorine and phosphorus.

The smooth curve obtained, as illustrated in FIG. 2, makes it possible to identify the ionic species of the phosphorus present on the surface 10 by the process of treatment of the invention.

A field-effect transistor, provided with a surface 10 treated with the iono-sensitive molecules of either Examples 1 or 2, was tested for sensitivity in a test medium comprising the following: for the acid pH values, the medium comprised a mixture of 0.01M acetic acid, 0.01M sodium acetate and 0.1M sodium nitrate in sufficient quantity of water; and, for the basic pH values, the medium comprised 2% tri hydroxymethylaminomethane with 0.5M KCl.

FIGS. 3 and 4 show the characteristic response curves obtained, showing two zones of inflexion at about pH 3.5–4 and 8, which are characteristic of the sensitivity of the grafted and operative surface gate.

FIG. 5 illustrates the response curves to the calcium ion in a 2% solution of tri hydroxymethylaminomethane with 0.5M KCl at pH 10, the sensor C$_1$ and C$_2$ prepared in accordance with Examples 1 and 2, in comparison with a sensor C$_0$ whose surface 10 is basic dielectric not treated in accordance with the invention. This FIG. illustrates a high sensitivity which may be considered as close for the sensors C$_1$ and C$_2$.

POSSIBILITY OF INDUSTRIAL APPLICATION

A sensor obtained by the process of the invention finds a typical application in the determination of the degree of water hardness.

The invention is not limited to the examples described and shown, as various modifications may be made thereto without departing from its scope.

We claim:

1. A process for making a surface gate of an integrated electrochemical sensor comprising a field-effect transistor having two doped zones comprising a source and a drain and a median surface on which a surface gate is to be formed, wherein the process comprises the steps of:

subjecting the median surface to a treatment of hydroxylation in order to obtain $10^{14}$ to $10^{15}$ OH sites per cm$^2$, washing and drying the surface, and further comprising the steps of:

grafting the median surface with a grafting product in order to produce grafts on some or all sites on the median surface, preparing phosphonate-based iono-sensitive molecules, making operative one or more of the grafts using the iono-sensitive molecules.

2. The process according to claim 1, wherein the grafting product is selected from pure silane, aminosilane, alkoxysilane, halosilane, of general formula:

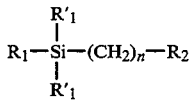

in which:
—R$_1$ is either:
—(CH$_3$)$_2$—N—,
—CH$_3$—O—,
—CH$_3$—CH$_2$—O—,
—Cl—,
—R′$_1$ is either:
—CH$_3$—,
—CH$_3$—O—,
—CH$_3$—CH$_2$—O—,
—R$_2$ is in all cases:
—Cl.

3. The process according to claim 1, wherein the step of grafting the surface comprises the following steps:
hydroxylation,
degassing in vacuo, and
reaction by immersion in the presence of the grafting product.

4. The process according to claim 3, wherein the degassing step comprises heating the surface to a temperature range of 120° to 160° C. for a duration of 1 to 5 hours in vacuo.

5. The process according to claim 3, wherein the grafting product is based on phosphonate, the surface is subjected to heating to a temperature range of 60° to 80° C. for a duration of 15 to 48 hours in an enclosure at ambient pressure in the presence of a neutral gas, and the surface is washed and dried.

6. The process according to claim 1, wherein the iono-sensitive molecules are characterized by a group (CH$_3$)$_2$—N—, a spacer group —(CH$_2$)$_n$, and a group containing phosphorus-oxygen bonds and selected from the group consisting of phosphonate, ethylphosphonate and phosphate.

7. The process according to claim 1, wherein the iono-sensitive molecules are selected from the group consisting of

  (1)

  (2)

8. The process according to claim 1, characterized in that the step of making operative one or more of the grafts comprises forming a mixture comprising 0.5 g of iono-sensitive molecules in 40 ml of methanol; and contacting the surface with the mixture, for 1 to 5 days, to a reflux temperature.

9. The process according to claim 8, characterized in that from 100 to 500 mg of sodium iodide is added to mixture comprising the iono-sensitive molecules and methanol.

10. An integrated electromechanical sensor comprising a field-effect transistor having a surface gate made in accordance with the process of claim 1, and characterized in that its pH response curve shows two zones of inflexion between pH 3 and 4 and pH 7 and 8, characteristic of the presence of phosphonate-based iono-sensitive molecules.

* * * * *